United States Patent [19]

Karkar et al.

[11] Patent Number: 4,745,279
[45] Date of Patent: May 17, 1988

[54] HEMATOCRIT MEASURING APPARATUS

[75] Inventors: Maurice N. Karkar; Warren M. Long, both of Costa Mesa; Stan O. Heinemann, Irvine, all of Calif.

[73] Assignee: American Hospital Supply Corporation, Deerfield, Ill.

[21] Appl. No.: 815,576

[22] Filed: Jan. 2, 1986

[51] Int. Cl.[4] .......................... G01J 1/00; G01N 33/48
[52] U.S. Cl. ........................................ 250/343; 356/40
[58] Field of Search .................... 250/343; 356/39, 41, 356/40, 446, 448, 411; 422/44, 45; 128/633, 634, 632

[56] References Cited

U.S. PATENT DOCUMENTS

| 3,684,450 | 8/1972 | Adler et al. | |
|---|---|---|---|
| 4,202,339 | 5/1980 | Wirtzfeld et al. | 128/634 |
| 4,243,883 | 1/1981 | Schwarzmann . | |
| 4,250,257 | 2/1981 | Lee et al. | |
| 4,283,143 | 8/1981 | Patterson . | |
| 4,303,336 | 12/1981 | Cullis | 356/39 |
| 4,444,498 | 4/1984 | Heinemann . | |
| 4,446,239 | 5/1984 | Tsuji et al. | |
| 4,447,150 | 5/1984 | Heinemann . | |
| 4,492,462 | 1/1985 | Pross et al. | |
| 4,521,521 | 6/1985 | Abbott et al. | |

OTHER PUBLICATIONS

IEEE: BME-17, No. 2, Apr. 1970, Author C. C. Johnson, pp. 129-133, "Optical Diffusion in Blood".
Medical & Biological Engineering & Computing: Jul. 1982, pp. 527-528, Authors: M. Singh & K. P. Joseph, "Optical Method for Haematocrit Determination".
29th ACEMB Sheraton-Boston, Boston, Mass., Nov. 6-10, 1976, Authors: Takatani, Cheung and Ko, "Estimation of Hemoglobin Concentration of Whole Blood Using Infrared Reflectance".

Primary Examiner—Janice A. Howell
Assistant Examiner—Richard E. Hanig
Attorney, Agent, or Firm—Weissenberger & Peterson

[57] ABSTRACT

The hematocrit of a volume of blood can be determined in real time without volume or flow rate limitations by sensing the diffusion of infrared light by the bloodstream. For this purpose, an infrared light beam is directed at a transparent cuvette through which the blood is conveyed, and a photodetector is mounted beside the cuvette at an angle such that the intersection of the light beam and of the principal sensitivity lobe of the detector is wholly spaced from the multiple scatter zone adjacent to the light source. The hematocrit signal produced by the photodetector can be corrected for the effect of oxygen saturation by providing an oxygen saturation signal, multiplying the hematocrit signal by a function of the oxygen saturation signal and using a look-up table to derive a linear true hematocrit signal. Means are also provided to compensate the detected hematocrit signal for the effects of temperature, drive current, and aging.

19 Claims, 6 Drawing Sheets

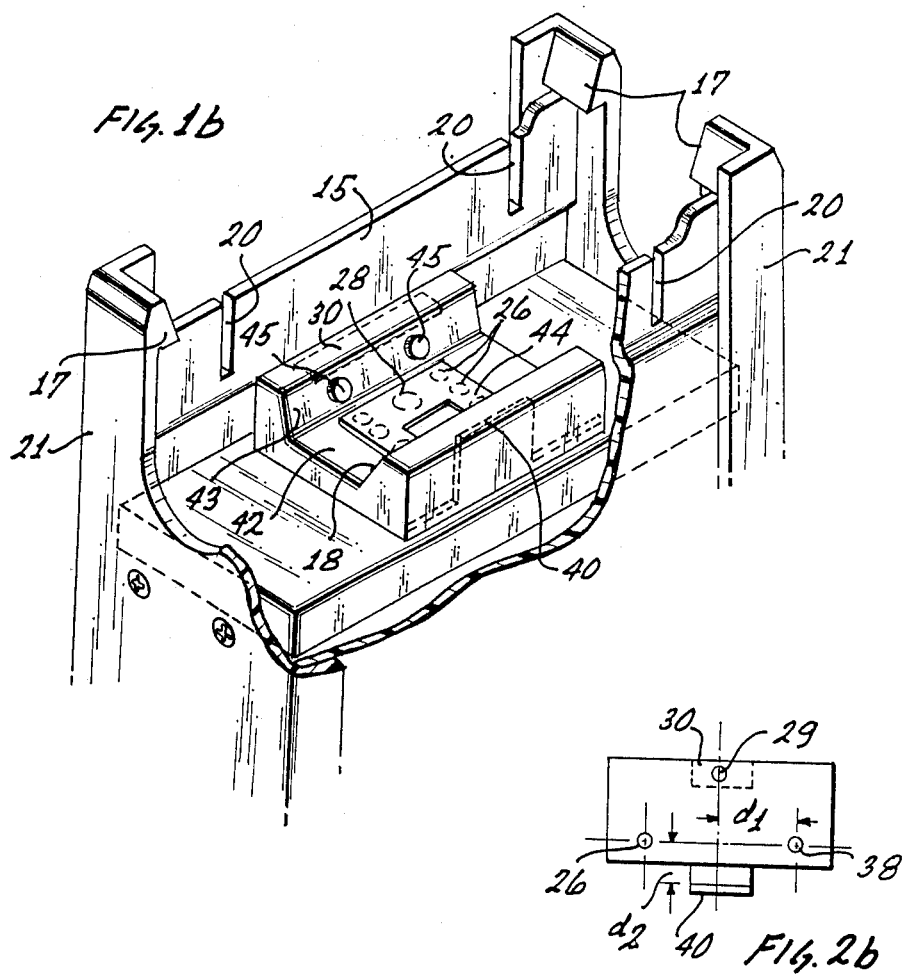
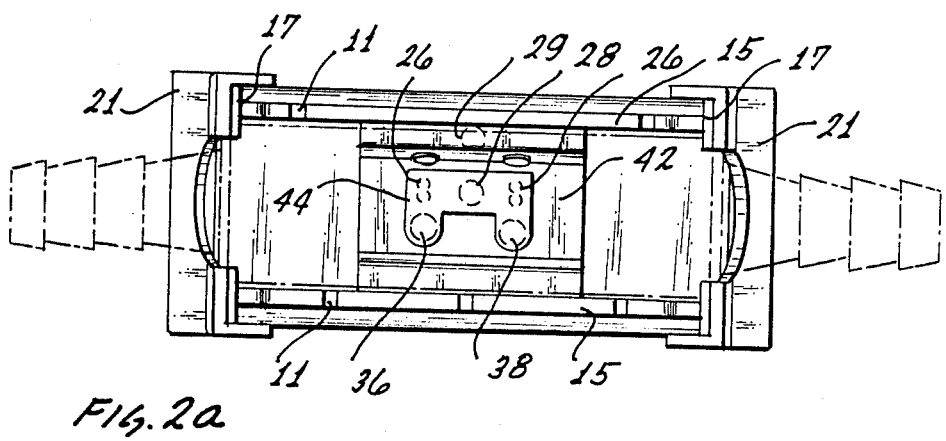

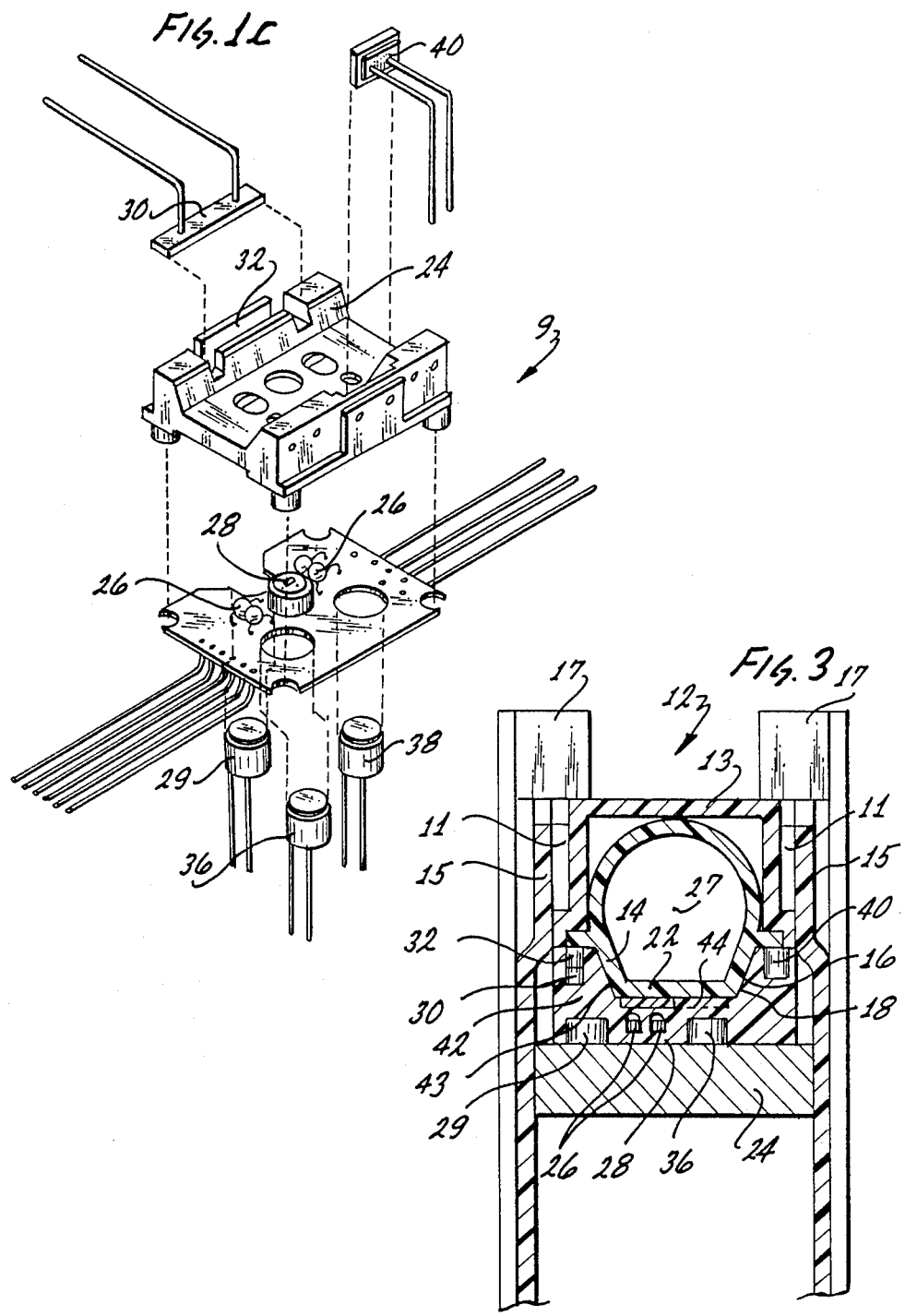

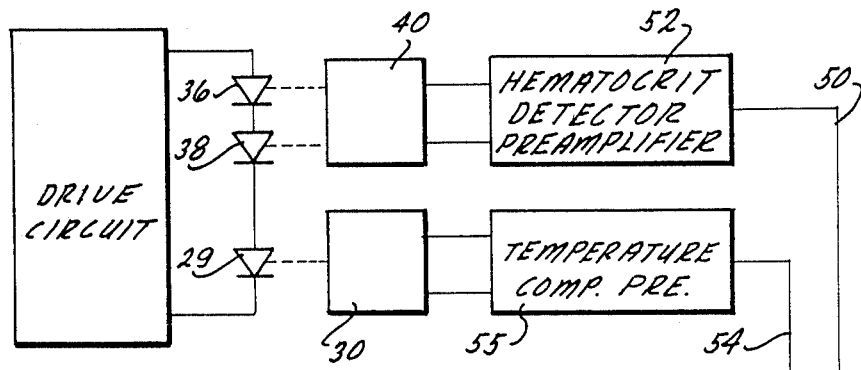
FIG. 4
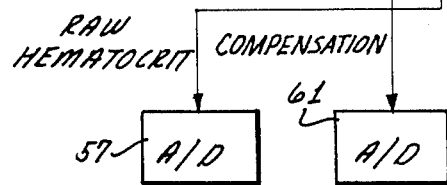
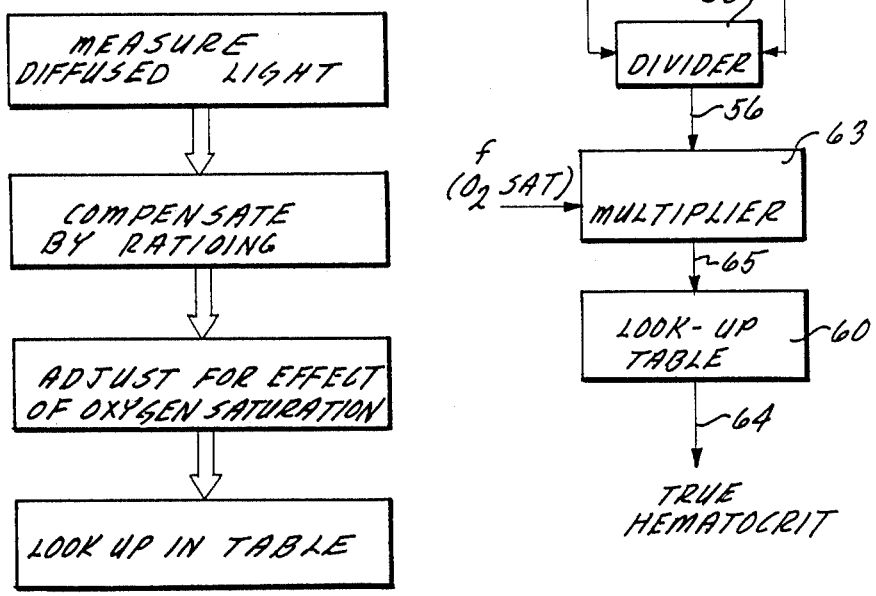
FIG. 6

HEMATOCRIT MEASURING APPARATUS

FIELD OF THE INVENTION

This application relates to apparatus for measuring hematocrit by diffusion scattering of infrared light by blood, and more particularly to an apparatus of that type which automatically compensates for oxygen saturation and is impervious to ancillary factors such as temperature and drive current variations, aging, and noise.

BACKGROUND OF THE INVENTION

Hematocrit is conventionally determined by centrifugation or by a Coulter counter which determines the number and size of erythrocytes in a given volume of blood. Both methods provide high accuracy but cannot produce a continuous real time measurement of a patient's hematocrit.

It has previously been proposed in U.S. Pat. No. 4,243,883 to monitor the hematocrit of a flowing bloodstream by measuring the transmission of infrared light at a wavelength of 800 nm through the bloodstream. At that wavelength, transmission of light through the bloodstream is independent of oxygen saturation. However, the wavelength is extremely critical, and precision light sources of this wavelength are very costly and difficult to obtain. In addition, transmission is limited to a bloodstream thickness of a few millimeters, which impedes the blood flow and limits the blood volume which can be handled.

It has also been proposed to measure hematocrit by reflection, but this method presents sensitivity problems when used over a wide range of hematocrits.

As shown in U.S. Pat. No. 4,447,150, apparatus has previously been devised for optically determining the oxygen saturation of a flowing blood stream by measuring the reflection of certain wavelengths of light by a bloodstream. It has, however, not been possible heretofore to continuously and instantaneously measure the hematocrit of the blood stream without volume or flow restrictions. In addition, the use of optical methods for hematocrit determination can introduce errors as a result of temperature differences, optical noise and factors relating to the emission characteristics of the light sources used in the apparatus.

SUMMARY OF THE INVENTION

The present invention provides an accurate and instantaneous measurement of hematocrit in a flowing blood mass (or, for that matter, in a stationary blood mass) of any volume which can be fully compensated for oxygen saturation and electro-optical error factors. This is accomplished by positioning an optical sensor adjacent a flowing blood stream or other large volume of blood in a position laterally spaced from an infrared light beam directed through the blood. This causes the sensor to detect the diffusion of light by the blood stream rather than its reflection or transmission. The diffusion measurement is preferable to a transmission measurement because it does not restrict the blood volume or flow conditions and is most sensitive to variations in hematocrit.

Connecting the diffusion sensor in series with a compensation sensor not exposed to the blood, and using a ratio of their readings as the raw hematocrit signal, makes it possible to create a structure in which the hematocrit measurement is unaffected by variations in ambient temperature, optical noise, drive current and aging of the light-emitting diodes.

The apparatus according to the invention produces separate hematocrit and oxygen saturation signals. The simultaneous measurement of hematocrit and oxygen saturation makes it possible to appropriately adjust the hematocrit signal for oxygen saturation on a continuing basis. This in turn permits design economies by allowing the use of readily available components at competitive cost. The amount of offset of the hematocrit measurement caused by variations in oxygen saturation at any given wavelength of illumination is mathematically expressible. The raw hematocrit measurement and the oxygen saturation measurement can therefore be mathematically combined, and the resulting saturation-adjusted hematocrit signal may be digitally supplied to an empirically determined lookup table to produce a linear true hematocrit output.

It is thus one object of the invention to produce a hematocrit measurement in real time by illuminating a volume of blood with infrared light, and measuring the diffusion scatter of that light by the blood mass.

It is a further object of the invention to provide an apparatus capable of accurately continuously measuring the hematocrit of a flowing blood stream at any level of oxygen saturation.

It is another object of the invention to provide an instrument of the type described which is impervious to temperature variation, optical noise, electrical variations and aging.

BRIEF DESCRIPTION OF THE DRAWINGS

FIG. 1b is a detailed partial perspective view of the probe of FIG. 1a with the cuvette removed;

FIG. 1c is an exploded view of the sensor assembly;

FIG. 2a is a plan view of the probe of FIG. 1b;

FIG. 2b is a location diagram of the diffusion-sensing elements;

FIG. 3 is a transverse vertical section of the probe of FIG. 1a;

FIG. 4 is a block diagram of the electro-optical circuit of the apparatus;

FIG. 6 is a flow chart of the digital signal processing portion of the apparatus of this invention;

DESCRIPTION OF THE PREFERRED EMBODIMENT

Figure 1A:
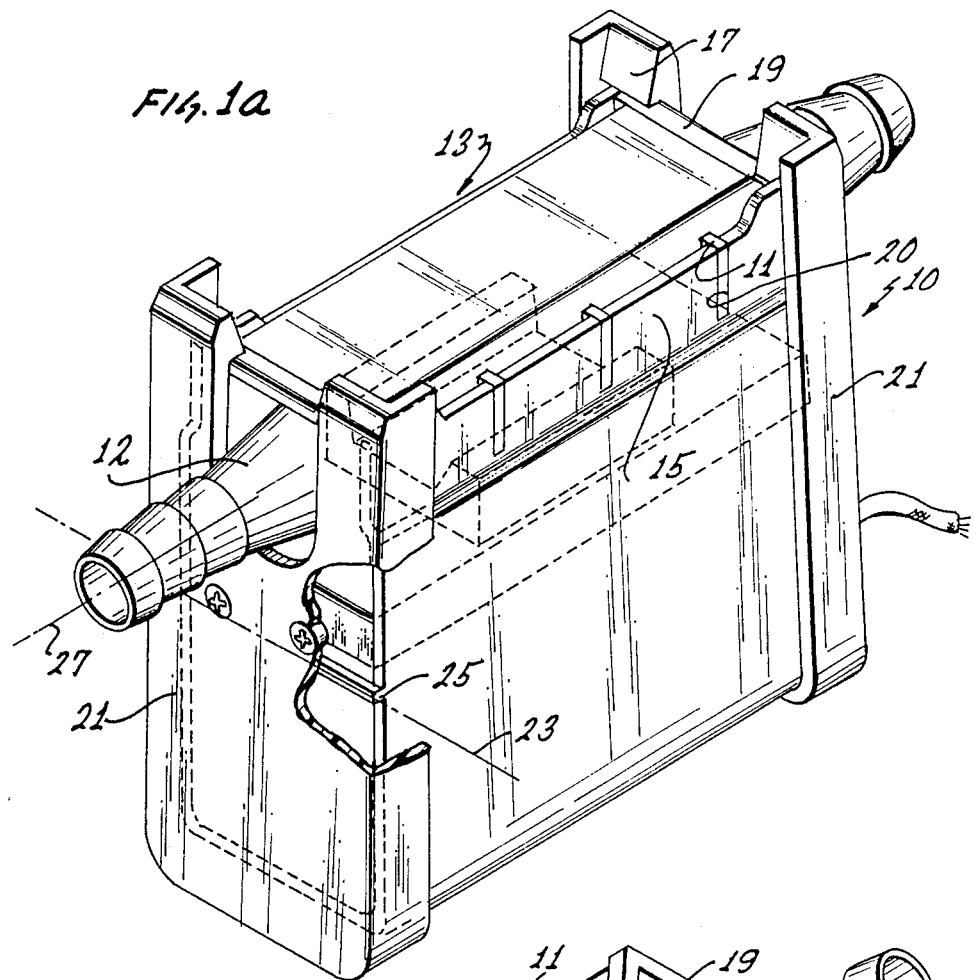
FIG 1a is a perspective view of the probe containing the bloodstream-carrying cuvette and the light sources and detectors.

FIG. 1a shows a probe 10 into which a cuvette 12 is inserted for the purpose of conveying a blood stream past the sensors which determine oxygen saturation and hematocrit. The cuvette 12 is firmly positioned against rotation and longitudinal movement by the engagement of tabs 11 on the cuvette cover 13 with slots 20 in the wall members 15 of the probe 10, and by engagement of the locking fingers 17 with the top end edges 19 of the cuvette cover 13. The cuvette cover 13 is preferably opaque so as to prevent ambient light from reaching the light sensors of the probe 10 when the cuvette 12 is inserted in the probe 10. The locking fingers 17 are part of the end plates 21 which are pivotable about a transverse axis such as 23. A resilient pad 25 biases the end plate 21 about axis 23 so as to urge the locking fingers 17 into the locking position. Blood is conveyed through the cuvette 12 by way of tubing (not shown) which may be appropriately connected to a patient's body during surgery.

Figure 7:
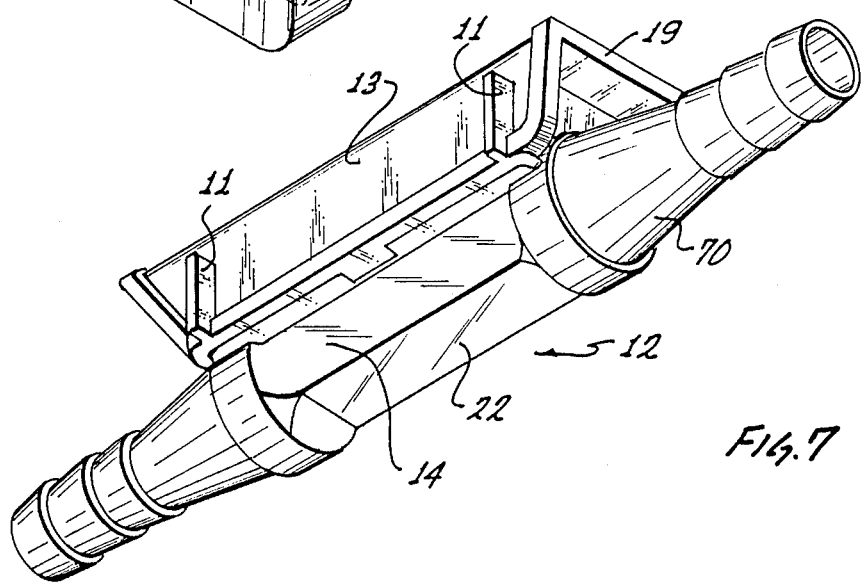
FIG. 7 is a perspective of the cuvette as seen from the underside.

As best seen in FIGS. 3 and 7, the cuvette 12 of this invention, which is formed of a transparent plastic material, has three flat sides 14, 16 and 22. Side 22 is horizontal when the cuvette 12 is in place in the probe 10, and lies against the pad 44 of the transparent, thermally conductive elastomeric encapsulation 42 of the probe 10. Side 16 is inclined and lies firmly against the inclined shoulder 18 when the cuvette 12 is fully inserted into the probe 10, held in alignment by the slots 20, and locked into place by the locking fingers 17. Side 14 seats against shoulder 43 of the encapsulation 42 but is not used for light transmission; however, its engagement with the resilient pads 45 (FIG. 1b) assists in biasing the side 16 into firm engagement with the shoulder 18.

FIG. 1c shows in greater detail the sensor assembly 9 which is at the heart of this invention. The sensor assembly 9 includes a sensor plate 24 of a hard plastic material in which light-emitting diodes (LEDs) 26 and a detector 28 are mounted directly underneath the flat side 22 of the cuvette 12 for the conventional measurement of oxygen saturation, in accordance with U.S. Pat. No. 4,447,150, by reflection of light from the blood stream in the cuvette 12. Another LED 29 is positioned in the sensor plate 24 in a position where its light does not impinge upon the cuvette 12. The LED 29 illuminates a compensation sensor 30 mounted in a slot 32 of the sensor plate 24. Because the LED 29 is exposed to the same temperature environment as the hematocrit LEDs discussed hereafter and can readily be fed by the same drive current, it can be used to provide automatic compensation for variations in those factors as herein explained. In view of the fact that the probe 10 would normally be replaced as a unit rather than repaired, the compensation LED 29 can also be expected to age at the same rate as the other LEDs of the system.

In accordance with the present invention, a pair of hematocrit LEDs 36, 38 are mounted in the sensor plate 24 beside the oxygen saturation LEDs 26. The beams of the hematocrit LEDs 36, 38 are directed vertically through the flat side 22 generally toward the axis 27 of the cuvette 12. To avoid interference between the oxygen saturation measurement and the hematocrit measurement, a timing circuit (not shown) switches rapidly back and forth between the oxygen saturation elements 26, 28 and the hematocrit elements 36, 38, 40 so that they are not both active at the same time.

As best seen in FIGS. 2b and 3, a hematocrit sensor 40 is embedded in the inclined shoulder 18 between the LEDs 36, 38. The sensor 40 is preferably somewhat recessed within the opaque shoulder 18, so that it will be exposed only to laterally directed light produced by diffusion scattering within the bloodstream in the cuvette 12.

In accordance with the invention, the wavelength of the LEDs 36, 38 would ideally be 805 nm because at that wavelength oxygen saturation has no effect on diffusion scattering. However, as a practical matter, commercial LEDs having wide bandwidth and nominal wavelengths somewhat different (e.g. ± a few percent) from that ideal are much less expensive and more readily available. Consequently, an adjustment of the raw hematocrit signal for oxygen saturation offset of the hematocrit measurement is economically advantageous in practice.

Like all the other components of the sensor assembly, the hematocrit sensor 40 is embedded in an elastomeric encapsulation 42 (FIG. 3) which provides close engagement between the assembly and the cuvette 12 and maintains all the components at an equal temperature due to its high heat conductivity. Firm engagement between the cuvette 12 and the hematocrit sensor 40 with minimal optical discontinuity is assured by the flat side 16 of the cuvette 12, whereas firm engagement of the flat side 22 with the horizontal surface of the encapsulation 42 is assured by a slightly elevated pad 44 in the resilient encapsulation 42.

Figure 8:
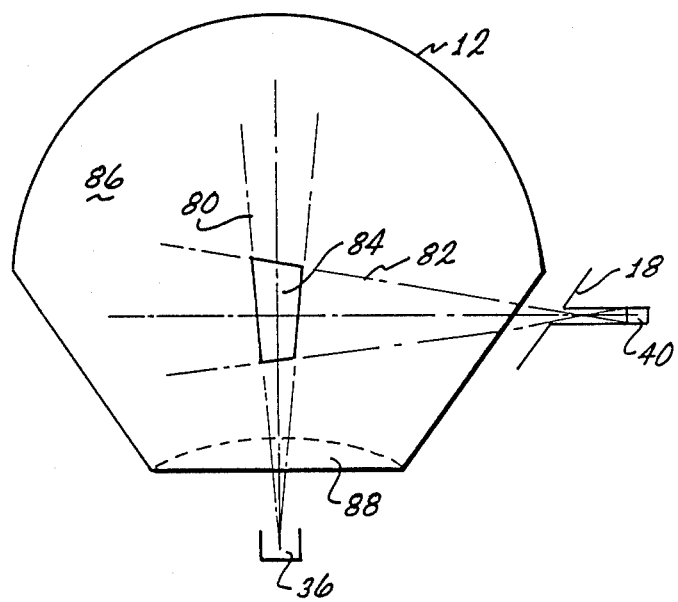
FIG. 8 illustrates the geometry of the optical elements for diffusion sensing.

FIG. 8 illustrates the use of diffusion scattering to measure hematocrit in accordance with this invention. According to Johnson, *Optical Diffusion in Blood*, IEEE Transactions on Bio-Medical Engineering, April, 1970, pp. 129–133, an infrared light beam directed at a volume of blood produces multiple scattering in an initially penetrated layer of about 1 mm thickness. As the light beam penetrates deeper into the blood volume, however, diffusion scattering begins to occur. This diffusion scattering results in the appearance of light patterns in the blood which vary quite significantly with variations in the hematocrit of the blood.

The sensor 40 detects these variations in the diffution light patterns and derives the raw hematocrit signal from them. Consequently, it is necessary that the sensor 40 be so placed that it will see only diffused light, not multiple-scattered or transmitted light. The requisite parameters for achieving this are shown in FIG. 8.

The light source 36 projects a beam 80 which is fairly well collimated. Likewise, the sensor 40, which is recessed behind the opaqued shoulder 18, has a limited field of view 82. In order for the sensor 40 to see substantially only diffused light, the intersection 84 of the beam 80 and view field 82 must lie wholly within the portion 86 of the blood volume in the cuvette which lies well above the multiple-scatter zone 88.

Referring now to FIG. 2b, the diffusion sensitivity is affected by the distance $d_2$. The smaller the distance $d_2$, the more illumination the sensor 40 will see; yet the distance $d_2$ is limited by the geometry of the cuvette 12.

In addition to the distance $d_2$, the distance $d_1$ also affects the hematocrit measurement. Specifically, the distance $d_1$ changes the shape and the sensitivity of the hematocrit calibration curve of FIG. 5b. The shorter the distance $d_1$, the more the calibration curve of FIG. 5b tends to be non-linear; on the other hand, the accuracy of the measurement is better for low values of $d_1$ at which the effects of the blood flow on the hematocrit measurement are minimized. As a practical matter, a $d_1$ value of 6 mm appears to be satisfactory.

Turning now to FIG. 4, it will be seen that the LEDs 36, 38 in the preferred embodiment are connected in series with the compensation LED 29. As a result, the hematocrit LEDs 36, 38 necessarily have the same driving current as compensation LED 29. Likewise, the LEDs 29, 36 and 38 (as well as the detectors 30 and 40) are all subjected to the same temperature and aging, and the LEDs 29, 36 and 38 are subjected to the same electrical noise.

The output signal 50 of the preamplifier 52 connected to the hematocrit sensor 40 is digitized by A/D converter 57, and its DC offset is removed by filter 59. The temperature compensation signal 54 is also digitized by A/D converter 61, and a ratio 56 of the signals 52 and 54 is formed by the divider 58. Because the signal 56 is a ratio whose numerator and denominator are equally affected by drive current and temperature variations as well as aging and noise, the signal 56 will be unaffected by any of those factors. In addition, the LEDs are preferably operated at intensities at which a drive current variation has the least effect on diffused light reception.

The compensated hematocrit signal 56 is now multiplied in multiplier 63 by an oxygen saturation factor. This operation takes the form $$H_{65} = H_{56}[k(100-OS)+1]$$

in which $H_{65}$ is the output of multiplier 63 appearing on line 65; $H_{56}$ is the temperature compensated hematocrit signal from line 56; k is a proportionality factor dependent upon the wavelength used and OS is the percentage of oxygen saturation measured by saturation sensor 28 and its associated conventional circuitry.

Figure 5A:
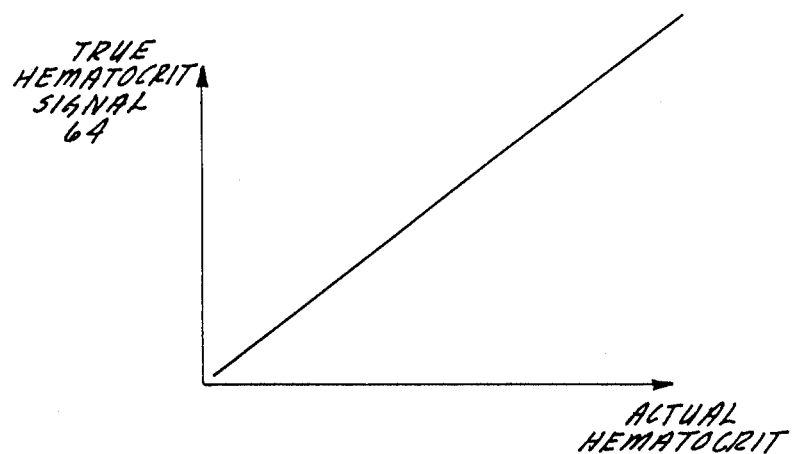
FIG. 5a is a graph showing the relationship of the true hematocrit signal produced by the apparatus of the invention as compared to actual hematocrit determined by a Coulter counter.
Figure 5B:
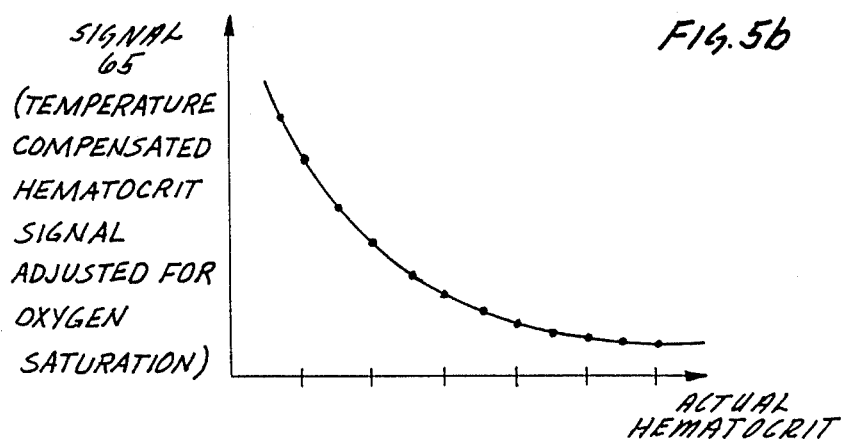
FIG. 5b is a graph showing the relation between the raw hematocrit signal of the apparatus of this invention and actual hematocrit.

The adjusted hematocrit signal $H_{65}$ is a non-linear function (FIG. 5b of the actual hematocrit which is valid for all practical values of oxygen saturation. Consequently, by applying this signal to a look-up table 60, a true hematocrit signal 64 can be produced which is a linear function of the actual hematocrit (FIG. 5a) and can therefore be used to operate a suitable display (not shown). It will be understood that although a digital look-up table is preferable because of its ready modifiability in production, analog or digital hardware may be used to accomplish the same result.

FIG. 6 is a self-explanatory flow chart illustrating the signal processing sequence described above.

FIG. 7 shows in detail the cuvette 12 used in this invention. The body 70 of the cuvette 12 is formed of a transparent, medical-grade plastic such as PMMA. The central portion of the cuvette 12 is larger in diameter than its ends, so as to reduce the velocity of the bloodstream as it passes the sensors of the probe 10. Within the central portion, the cuvette 12 is rounded at the top (FIG. 3) but has three flat sides 14, 16 and 22 (only two of which are visible in FIG. 7) for the purposes previously described herein.

The cuvette 12 is provided with an opaque cover 13 of generally U-shaped cross section which serves the dual function of preventing ambient light from reaching the sensors of the probe and interfering with their performance, and of properly positioning the cuvette 12 in the probe 10. For the latter purpose, the engagement of the vertical sides of the cover 13 with the walls 15 of the probe 10 prevents any rotational mispositioning of the cuvette 12 about its axis, so that firm engagement of the flat sides 16, 22 with the encapsulation 42 (FIG. 3) is assured.

Although this is not necessary if the cuvette 12 is symmetrical, the cuvette 12 is made insertable in only one direction by providing one side of the probe 10 and one side of the cover 13 with two tabs 11 and matching slots 20 (FIGS. 1b and 7), and the other side with three (FIG. 1a).

We claim:

1. Apparatus for measuring the hematocrit of a flowing bloodstream in real time, comprising:
    (a) transparent cuvette means for containing said flowing bloodstream;
    (b) infrared light source means adjacent said cuvette means for illuminating said bloodstream;
    (c) detector means adjacent said cuvette means for detecting said infrared light after diffusion thereof by said bloodstream; and
    (d) signal-producing means for producing a hematocrit signal which is a predetermined function of said detected diffused light;
    (e) second detector means for compensating said first-named detector means; and
    (f) second light source means for directly illuminating the said second detector means, said second light source and said first-named light source being connected in series;
    (g) said signal-producing means being arranged to produce a hematocrit signal which is a function of the ratio of the light values senses by said first-named and second detector means, respectively.

2. The apparatus of claim 1, further comprising means for maintaining said first and second detector means at substantially the same temperature.

3. Apparatus for measuring the hematocrit of a flowing bloodstream in real time, comprising:
    (a) first means for producing a first hematocrit signal which is a function of the diffusion of an infrared light beam by said bloodstream;
    (b) second means for producing a signal representative of the oxygen saturation of said bloodstream;
    (c) third means for multiplying said first hematocrit signal by a function of said oxygen saturation signal to produce an adjusted hematocrit signal; and
    (d) look-up table means for producing a linear hematocrit signal from predetermine combinations of said first hematocrit and oxygen saturation signal.

4. The apparatus of claim 3, in which said first means include a first light source and a first photodetector positioned to see only light diffused by said bloodstream; and said second means include a second light source and a second photodetector positioned to see light multiplescattered by said bloodstream.

5. The apparatus of claim 4, in which said first light source and first photodetector are active at different times than said second light source and photodetector.

6. The apparatus of claim 4, further comprising:
    (e) a third light source and a third photodetector positioned to see only said third light source;
    (f) said first and third light sources being connected in series, and said first hematocrit signal being a function of the ratio of the light values detected by said first and third photodetectors.

7. Apparatus for measuring the hematocrit of a flowing bloodstream in real time, comprising:
    (a) a cuvette adapted to have a bloodstream flowing therethrough, said cuvette having a longitudinal axis;
    (b) a holder for receiving said cuvette;
    (c) first light source and photodetector means mounted, respectively, in said holder so as to detect only diffused light;
    (d) second light source and photodetector means mounted in said holder so as to detect multiple-scattered light;

(e) third light source and photodetector means mounted in said holder in a position to only see each other; and (f) resilient, transparent, thermally conductive encapsulation means for providing a seat for positioning said cuvette in said holder, said encapsulation means enclosing all of said light source and photodetector means and maintaining them at substantially the same temperature.

8. The apparatus of claim 7, in which said cuvette has a substantially flat side surface, said encapsulation means have an inclined side surface adapted to mate with said flat surface, and said first photodetector means are positioned within said inclined surface.

9. The apparatus of claim 8, in which said cuvette further has a substantially flat bottom surface, said encapsulation means have a substantially horizontal surface adapted to mate with said flat bottom surface, and said second light source means photodetector means are positioned within said horizontal surface.

10. The apparatus of claim 9, in which said first light source means are also positioned within said horizontal surface.

11. The apparatus of claim 7, in which said holder has a wall including slots, said cuvette includes matching tabs, and said slots and tabs cooperate to hold said cuvette against rotation in said holder.

12. The apparatus of claim 7, in which said encapsulation means have a horizontal surface including an elevated portion for contacting said cuvette immediately above said first and second light source and said second photodetector means.

13. A cuvette for use in determining the hematocrit of a flowing bloodstream as a function of oxygen saturation, comprising:
    (a) a substantially cylindrical body having a central portion with a plurality of longitudinally extending flat sides forming an acute angle with each other, and
    (b) an opaque cover fixed with respect to said body on the side opposite said flat sides.

14. The cuvette of claim 13, in which said cover is generally U-shaped and carries positioning tabs on the legs of said U for longitudinal positioning of said cuvette within a probe.

15. The cuvette of claim 14, in which one leg of said U carries a different number of said positioning tabs than the other leg.

16. Apparatus for measuring the hematocrit of a flowing bloodstram in real time, comprising:
    (a) transparent cuvette means for containing said flowing bloodstream;
    (b) infrared light source means adjacent said cuvette means for illuminating said bloodstream;
    (c) detector means adjacent said cuvette means for detecting said infrared light after diffusion thereof by said bloodstream;
    (d) signal-producing means for producing a hematocrit signal which is a predetermined function of said detected diffused light; and
    (e) said infrared light source means being arranged to emit a beam of light, said detector means having a restricted field of vision, and the intersection of said beam and field being sufficiently deep within said bloodstream to cause said detector means to see substantially only light diffused by said bloodstream.

17. The apparatus of claim 16, in which said intersection is substantially spaced from the multiple scatter zone of said bloodstream.

18. A method for measuring the hematocrit of a flowing bloodstream in real time, comprising the steps of:
    (a) illuminating said bloodstream with light;
    (b) detecting a first portion of said light diffused by said bloodstream;
    (c) detecting a second portion of said light multiple-scattered by said bloodstream;
    (d) producing an oxygen saturation signal which is a function of said detected multiple-scattered light portion;
    (e) producing a first hematocrit signal which is a function of said detected diffused light portion; and
    (f) using said oxygen saturation signal to adjust said first hematocrit signal so as to produce a second hematocrit signal which is independent of oxygen saturation.

19. The method of claim 18, in which said adjustment of said first hematocrit signal is a multiplication, and said second hematocrit signal is linearized by the use of a predetermined look-up table.

* * * * *